(12) United States Patent
Kubota et al.

(10) Patent No.: US 7,081,256 B2
(45) Date of Patent: Jul. 25, 2006

(54) QUINOLINONE DERIVATIVE PHARMACEUTICAL COMPOSITON AND PRODUCTION METHOD THEREFOR

(75) Inventors: Ryuji Kubota, Tokyo (JP); Hiroshi Araya, Gotenba (JP); Kouki Obata, Gotenba (JP); Nobuyuki Kimura, Sakura (JP); Hiroyuki Fukui, Chiba (JP); Hidetsugu Takagaki, Sakura (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 464 days.

(21) Appl. No.: 10/171,982

(22) Filed: Jun. 17, 2002

(65) Prior Publication Data

US 2003/0130310 A1    Jul. 10, 2003

(30) Foreign Application Priority Data

Jun. 20, 2001 (JP) ............................ 2001-187138

(51) Int. Cl.
*A61K 9/14* (2006.01)
*A61K 9/16* (2006.01)
*A61K 31/47* (2006.01)

(52) U.S. Cl. ...................... 424/494; 424/489; 424/490; 514/311

(58) Field of Classification Search ................ 424/489, 424/490, 494, 495; 514/311
See application file for complete search history.

(56) References Cited

U.S. PATENT DOCUMENTS

| 4,526,894 A | 7/1985 | Enomoto et al. ............ 514/312 |
| 5,318,971 A | 6/1994 | McCombie .................. 514/254 |
| 5,942,521 A | 8/1999 | Takagaki et al. |
| 6,242,425 B1 * | 6/2001 | Takagaki et al. .............. 514/25 |
| 6,627,642 B1 * | 9/2003 | Kimura et al. ............... 514/311 |

FOREIGN PATENT DOCUMENTS

| EP | 0 785 190 A2 | 7/1997 |
| EP | 0 927 718 A1 | 7/1999 |
| EP | 0 933 378 A1 | 8/1999 |
| EP | 1 129 712 A1 | 9/2001 |
| JP | 9-255659 | 9/1997 |
| JP | 11-255649 | 9/1999 |
| JP | 11255649 | * 9/1999 |
| JP | 2001-72593 | 3/2001 |
| JP | 91113054 | 11/2003 |
| WO | WO 01/19368 A1 | 3/2001 |

OTHER PUBLICATIONS

Aoki, Y. et al.; "*Inhibitory effect of a novel quinolinone derivative, TA-270, on asthmatic inflammatory responses in sensitized guinea pigs*"; European Journal of Pharmacology, vol. 409, No. 3, Dec. 15, 2000; pp. 325-330.

Proceedings of the 12th Annual Convention of the Japan Pharmaceutical Society, published on Mar. 14, 1997, and a Concise Explanation of Relevance.

* cited by examiner

*Primary Examiner*—Michael G. Hartley
(74) *Attorney, Agent, or Firm*—Armstrong, Kratz, Quintos, Hanson & Brooks, LLP (57) ABSTRACT

A quinolinone derivative pharmaceutical composition comprising a quinolinone derivative represented by the structural formula (I):

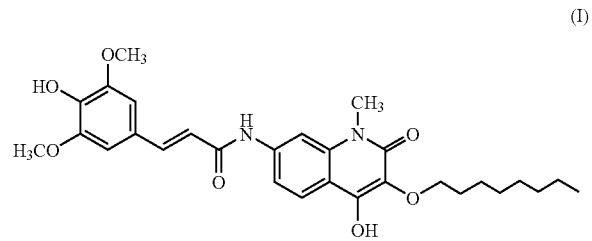

wherein the quinolinone derivative is in the form of particles, which have an average particle diameter of 0.5 to 10 μm and such a particle size distribution that particles having a particle diameter of 15 μm or less account for 90% or more of the totality of the particles, and also have a fusion enthalpy of 30 J/g or more, and the surface of the particles are coated with a water-soluble composition containing a water-soluble polymer, can quickly dissolve an active ingredient in the digestive tract and is also superior in long-term storage stability.

9 Claims, 5 Drawing Sheets

- □ HPC GRANULES (Example 2)
- ◇ HPMC GRANULES (Example 3)
- ○ PULLULAN GRANULES (Example 4)
- △ CMC-Na GRANULES (Example 5)
- ■ PVP GRANULES (Example 6)
- ◆ GROUND POWDERS (Comparative Example 3)

QUINOLINONE DERIVATIVE PHARMACEUTICAL COMPOSITON AND PRODUCTION METHOD THEREFOR

BACKGROUND OF THE INVENTION

1. Field of the Invention

The present invention relates to a pharmaceutical composition containing a quinolinone derivative, which is useful as an anti-allergy agent, and to a production method therefor.

2. Description of Related Art

A quinolinone derivative represented by the structural formula (I):

is a compound disclosed in Japanese Unexamined Patent Application, First Publication No. Hei 9-255659 (corresponding U.S. Pat. No. 5,942,521) and is useful as an anti-allergy agent which has low toxicity in the living body and is particularly effective against immediate allergy diseases and delayed allergy diseases such as immediate type asthma, delayed type asthma, bronchial asthma, pediatric asthma, hypersensitivity pneumonitis, atopic dermatitis, allergic dermatitis, urticaria, eczema, allergic conjunctivitis, allergic rhinitis, hay fever, food allergy, allergic gastroenteritis, allergic colitis, contact dermatitis, and autoimmune diseases.

However, since the quinolinone derivative is a slightly soluble drug, the dissolution rate of a pharmaceutical preparation produced by the method described in the publication described above in the digestive tract is not always satisfactory and an absorption ratio and an absorption rate are likely to change. Therefore, it has been required to develop a pharmaceutical composition wherein the dissolution rate of the quinolinone derivative in the digestive tract is improved, thereby improving the absorbability.

On the other hand, Japanese Unexamined Patent Application, First Publication No. Hei 11-255649 describes that the quinolinone derivative is polymorphism in its crystal form and includes four kinds of crystal forms such as α-type crystal, β-type crystal, γ-type crystal and δ-type crystal and, particularly, β-type crystal and γ-type crystal are superior in bioabsorbability to the α-type crystal. The same publication describes that particles obtained by grinding the quinolinone derivatives in the respective crystal forms for about 10 minutes using an automatic agate mortar have improved bioabsorbability as compared with the bioabsorbability before grinding. However, when the quinolinone derivative is ground by such a method, there arose a problem that the crystallinity of the quinolinone derivative is lowered and, as a result, the physicochemical stability of the resulting quinolinone derivative is lowered.

BRIEF SUMMARY OF THE INVENTION

Objects to be achieved by the present invention is to provide a quinolinone derivative pharmaceutical composition which can quickly dissolve an active ingredient in the digestive tract and is also superior in long-term storage stability, and to provide a production method therefor.

To achieve the objects described above, the present inventors have intensively researched and found that the dissolution rate in the digestive tract is improved and the long-term storage stability is also improved by grinding the quinolinone derivative into particles, which have an average particle diameter of 0.5 to 10 μm and such a particle size distribution that particles having a particle diameter of 15 μm or less account for 90% or more of the totality of the particles, while maintaining its fusion enthalpy at a high level and further coating the resulting particles with a water-soluble composition containing a water-soluble polymer. Thus, the present invention has been completed.

To achieve the object described above, the present invention provides a quinolinone derivative pharmaceutical composition comprising a quinolinone derivative represented by the structural formula (I):

wherein the quinolinone derivative is in the form of particles, which have an average particle diameter of 0.5 to 10 μm and such a particle size distribution that particles having a particle diameter of 15 μm or less account for 90% or more of the totality of the particles, and also have a fusion enthalpy of 30 J/g or more, and the surface of the particles are coated with a water-soluble composition containing a water-soluble polymer.

To achieve the object described above, the present invention provides a process for producing a quinolinone derivative pharmaceutical composition, which comprises the first step of grinding a quinolinone derivative represented by the structural formula (I) described above into particles, which have an average particle diameter of 0.5 to 10 μm and such a particle size distribution that particles having a particle diameter of 15 μm or less account for 90% or more of the totality of the particles, and also have a fusion enthalpy of 30 J/g or more; and the step of coating the particles obtained in the first step with a water-soluble composition containing a water-soluble polymer.

Since the pharmaceutical composition of the present invention can quickly dissolve the quinolinone derivative represented by the structural formula (I) in the digestive tract and is also superior in storage stability, it is useful as a preparation of an anti-allergy agent which is particularly effective against immediate allergy diseases and delayed allergy diseases such as immediate type asthma, delayed type asthma, bronchial asthma, pediatric asthma, hypersensitivity pneumonitis, atopic dermatitis, allergic dermatitis, urticaria, eczema, allergic conjunctivitis, allergic rhinitis, hay fever, food allergy, allergic gastroenteritis, allergic colitis, contact dermatitis, and autoimmune disease.

Japanese Unexamined Patent Application, First Publication No. Hei 9-255659 and U.S. Pat. No. 5,942,521 are incorporated herein by reference.

DETAILED DESCRIPTION OF THE INVENTION

As used herein, the expression "quinolinone derivative is in the form of particles, which have an average particle diameter of 0.5 to 10 μm and such a particle size distribution that particles having a particle diameter of 15 μm or less account for 90% or more of the totality of the particles" means that a mass median aerodynamic diameter in the volume-basis distribution obtained, when the particle size distribution of the quinolinone derivative is measured by an aerodynamic flight time type dry particle size distribution measuring apparatus (AEROSIZER: Central Scientific Commerce, Inc.), is within a range from 0.5 to 10 μm and the particles have such a particle size distribution that particles having a particle diameter of 15 μm or less account for 90% or more of the totality of the particles.

Although the crystal form of the quinolinone derivative used in the present invention is not specifically limited, the quinolinone derivative is preferably composed of the β-type crystal or γ-type crystal so that the pharmaceutical composition of the present invention has better absorbability in the living body and stability. Such polymorphism can be specified by the measurement of powder X-ray diffraction patterns and differential scanning calorimetry (DSC).

The quinolinone derivative used in the present invention is in the form of particles having an average particle diameter within a range from 0.5 to 10 μm, and preferably from 1 to 5 μm. When the average particle diameter is less than 0.5 μm, the physicochemical stability of the quinolinone derivative is drastically lowered. On the other hand, when the average particle diameter exceeds 10 μm, the quinolinone derivative is difficult to dissolve quickly in the living body.

The quinolinone derivative used in the present invention has such a particle size distribution that particles having a particle diameter of 15 μm or less, and preferably 10 μm or less, account for 90% or more of the totality of the particles. When particles having and a particle diameter of more than 15 μm account for 10% or more of the totality of the particles, the quinolinone derivative is difficult to dissolve quickly in the living body.

Furthermore, the quinolinone derivative used in the present invention has a fusion enthalpy (ΔH) of 30 J/g or more, and preferably 35 J/g or more. When the fusion enthalpy is less than 30 J/g, the physicochemical stability of the quinolinone derivative is drastically lowered. As used herein, the term "fusion enthalpy" refers to a value obtained from an endothermic peak due to fusion of the quinolinone derivative crystal in differential scanning calorimetry (DSC) and is an index of the crystallinity.

The quinolinone derivative used in the present invention is obtained by further coating the particles ground into the state as described above with a water-soluble composition containing a water-soluble polymer. When the particle diameter and fusion enthalpy of the quinolinone derivative used in the present invention meet the above conditions, the surface of such a quinolinone derivative has high hydrophobicity and the dissolution rate in the living body is not deemed to be satisfactorily high. However, the wettability is improved by coating the surface with the water-soluble composition containing a water-soluble polymer, thereby making it possible to quickly dissolve the quinolinone derivative.

Preferred examples of the water-soluble polymer include, but are not limited to, cellulose derivative such as hydroxypropyl cellulose (HPC), hydroxypropylmethyl cellulose (HPMC), methyl cellulose, sodium carboxymethyl cellulose (CMC-Na), or hydroxyethyl cellulose; synthetic polymer such as polyvinyl pyrrolidone or polyvinyl alcohol; and starch derivative such as pullulan or dextrin. Among these water-soluble polymers, cellulose derivative such as hydroxypropyl cellulose, hydroxypropylmethyl cellulose, methyl cellulose, sodium carboxymethyl cellulose or hydroxyethyl cellulose is preferred, and hydroxypropyl cellulose, hydroxypropylmethyl cellulose or sodium carboxymethyl cellulose is more preferred.

These water-soluble polymers may be used alone and, if necessary, two or more kinds thereof may be used in combination.

The amount of the water-soluble polymer in the present invention is not specifically limited, but is preferably within a range from 0.5 to 12 parts by weight, and more preferably from 1 to 10 parts by weight, based on 100 parts by weight of the quinolinone derivative. When using two or more kinds of these water-soluble polymers in combination, the total amount of the water-soluble polymers is preferably within a range from 0.5 to 12 parts by weight, and more preferably from 1 to 10 parts by weight, based on 100 parts by weight of the quinolinone derivative.

When the amount of the water-soluble polymer is less than 0.5 parts by weight based on the quinolinone derivative, the wettability of the quinolinone derivative is not satisfactorily improved and no quick dissolution rate tends to be obtained. On the other hand, when the amount exceeds 12 parts by weight, although the wettability is satisfactorily improved, the dissolution time of the coated water-soluble polymer itself is prolonged and no quick dissolution rate of the quinolinone derivative tends to be obtained.

It is preferred that the water-soluble composition used in the present invention further contain surfactants. The use of the surfactant to coat the surface of the quinolinone derivative, together with the water-soluble polymer, imparts better dissolution properties of the quinolinone derivative in the living body.

Examples of the surfactant include sucrose fatty acid ester, polyoxyethylene hardened castor oil, polyoxyethylene fatty acid ester, polyoxyethylene glycol, polyoxyethylene sorbitan fatty acid ester, alkyl sulfate, alkylbenzene sulfonate, and sulfosuccinate ester salt.

Among these surfactants, anionic surfactants such as alkyl sulfate, alkylbenzene sulfonate and sulfosuccinate ester salt are more preferred. Examples of the alkyl sulfate ester salt include sodium lauryl sulfate, and examples of the sulfosuccinate ester salt include dioctyl sodium sulfosuccinate. These surfactants may be used alone and, if necessary, two or more kinds thereof may be used in combination.

The amount of the surfactant is preferably within a range from 0.1 to 20 parts by weight, and more preferably from 0.1 to 10 parts by weight, based on 100 parts by weight of the quinolinone derivative. When using two or more kinds of these surfactants in combination, the total amount of these surfactants is preferably within a range from 0.1 to 20 parts by weight, and more preferably from 0.1 to 10 parts by weight, based on 100 parts by weight of the quinolinone derivative.

Although the pharmaceutical composition of the present invention exhibits satisfactorily quick dissolution rate as it is, disintegrators are preferably added to further enhance the dissolution rate. Examples of the disintegrator include starch and a derivative thereof, such as cornstarch, hydroxypropyl starch, carboxymethyl starch sodium, or partially pregelatinized starch; cellulose and a derivative thereof, such as carmellose, carmellose calcium, croscarmellose sodium, or low-substitution-degree hydroxypropyl cellulose; and synthetic polymer such as crospovidone. Among these disintegrators, croscarmellose sodium, low-substitution-degree hydroxypropyl cellulose, carmellose calcium, sodium carboxymethyl starch and crospovidone are preferred. These disintegrators may be used alone and, if necessary, two or more kinds thereof may be used in combination.

The amount of the disintegrator is preferably within a range from 1 to 30 parts by weight, and more preferably from 3 to 20 parts by weight, based on 100 parts by weight of the quinolinone derivative. When using two or more kinds of these disintegrators in combination, the total amount of these disintegrators is preferably within a range from 1 to 30 parts by weight, and more preferably from 3 to 20 parts by weight, based on 100 parts by weight of the quinolinone derivative.

The pharmaceutical composition of the present invention obtained by the method described above may contain the quinolinone derivative as the active ingredient. Although the specific formulation and dosage form are not specifically limited, excipients, disintegrators, binders, lubricants, surfactants, coating agents, antioxidants, perfumes and colorants are added to the pharmaceutical composition and the resulting mixture is formed into preparations having the dosage forms such as powders, granules, dry syrups, tablets, chewable tablets, troches, effervescent tablets, capsules, and pills. In the process for producing the pharmaceutical composition, there can be employed appropriate methods, which can be used by a person skilled in the art, according to the aspect of the pharmaceutical composition.

Examples of the excipient include starch and derivatives thereof (e.g., dextrin, carboxymethyl starch, etc.), cellulose and derivatives thereof (e.g., methyl cellulose, hydroxypropylmethyl cellulose, etc.), saccharides (e.g., lactose, D-mannitol, glucose, etc.), silicic acid and silicates (e.g., natural aluminum silicate, magnesium silicate, etc.), carbonate (e.g., calcium carbonate, magnesium carbonate, dibasic sodium carbonate, etc.), aluminum magnesium hydroxide, synthetic hydrotalcite, polyoxyethylene derivative, glycerin monostearate, and sorbitan monooleate.

Examples of the binder include starch and a derivative thereof (e.g., pregelatinized starch, dextrin, etc.), cellulose and a derivative thereof (e.g., ethyl cellulose, sodium carboxymethyl cellulose, hydroxypropylmethyl cellulose, etc.), gum arabic, tragacanth, gelatin, saccharides (e.g., glucose, sucrose, etc.), ethanol, and polyvinyl alcohol.

Examples of the lubricant include stearic acid, hardened oil, calcium stearate, magnesium stearate, talc, silicic acid and salts thereof (e.g., light anhydrous silicic acid, natural aluminum silicate, etc.), titanium oxide, dibasic calcium phosphate, dry aluminum hydroxide gel, and macrogol.

Examples of the coating agent include cellulose derivative (e.g., hydroxypropyl cellulose, hydroxypropylmethyl cellulose, cellulose acetate phthalate, hydroxypropylmethyl cellulose phthalate, etc.), shellac, polyethylene glycols, polyvinyl pyrrolidone, polyvinyl pyrrolidones (e.g., poly-2-vinylpyridine, poly-2-vinyl-5-ethylpyridine, etc.), polyvinyl acetyldiethylamino acetate, polyvinyl alcohol phthalate, and methacrylate-methacrylic acid copolymer.

Examples of the antioxidant include sulfites (e.g., sodium sulfite, sodium bisulfite, etc.), rongalite, erythrobic acid, L-ascorbic acid, cysteine, thioglycerol, butylhydroxyanisole, dibutylhydroxytoluene, propyl gallate, palmitate ascorbate, and dl-α-tocopherol.

Examples of the perfume include dl-menthol, l-menthol, sugar flavor, mint flavor, vanilla flavor, bitter orange peel oil, peppermint oil, eucalyptus oil, and cinnamon bark oil.

Examples of the colorant include indigo carmine, caramel, riboflavin, food tar pigment, iron oxide, titanium oxide, β-carotene, chlorophyll, and lake pigment.

The content of the quinolinone derivative represented by the structural formula (I) in the pharmaceutical composition of the present invention varies depending on the dosage form, but is preferably within a range from 0.01 to 99.5% by weight.

Next, the process for producing the quinolinone derivative pharmaceutical composition of the present invention will be described.

First, the first step in the process of the present invention will be described.

The quinolinone derivative produced by the method described in "DESCRIPTION OF RELATED ART" is usually in the form of particles having an average particle diameter within a range from about 20 to 150 μm. However, it is difficult to dissolve particles having such a particle diameter in the living body.

Any apparatus can be used to grind the quinolinone derivative as long as the apparatus can grind the quinolinone derivative into particles having an average particle diameter of 0.5 to 10 μm and having a particle size distribution such that particles having a particle diameter of 15 μm or less account for 90% or more of the totality of the particles, while the apparatus can maintain a fusion enthalpy of the ground quinolinone derivative particles at a high level. Examples thereof include impact type grinder (hammer mill), ball mill, wet grinder and jet grinder. Among these apparatuses, a jet grinder is preferably used. The use of the jet grinder makes it possible to grind under comparatively mild conditions in the case of grinding of the crystal and to grind while maintaining the fusion enthalpy of the crystal at a high level.

Japanese Unexamined Patent Application, First Publication No. Hei 11-255649 describes that the bioabsorbability is improved by grinding the quinolinone derivative for about 10 minutes using an automatic agate mortar. However, the crystallinity of the quinolinone derivative crystal ground under these grinding conditions is lowered and the fusion enthalpy is reduced to 30 J/g or less, resulting in poor stability. However, according to the grinding method, the quinolinone derivative can be ground while maintaining the fusion enthalpy at a high level.

Next, the second step of the present invention will be described.

The method of coating the particles obtained in the first step is not specifically limited as long as it is a method capable of producing a composition wherein all or a portion of the surface of particles of the quinolinone derivative is coated with a water-soluble composition containing a water-soluble polymer. Examples thereof include (1) a method of mixing a solution, which is prepared by dissolving a water-soluble composition containing a water-soluble polymer in water or a proper organic solvent, with a quinolinone derivative, followed by wet granulation and further drying, (2) a method of spray-coating a water-soluble composition containing a water-soluble polymer, which is prepared by dissolving a quinolinone derivative as nuclear particles in water or a proper organic solvent, and (3) a method of dispersing a quinolinone derivative in a water-soluble composition containing a water-soluble polymer, which is prepared by dissolving in water or a proper organic solvent, and spray-drying the resulting dispersion. Among these methods, the method (1) is preferred.

The dose of the pharmaceutical composition of the present invention can be appropriately decided according to the severity of each disease, age, administration method and doctor's judgment. For example, the quinolinone derivative represented by the structural formula (I) is preferably administered at a dose of from 0.1 to 2000 mg per day per kg body weight. The daily dose of the pharmaceutical composition of the present invention may be used in one portion during 1 to 7 days or be divided into portions in accordance with the severity of disease and doctor's judgment.

EXAMPLES

The present invention will be described in more detail by way of Examples and Comparative Examples; however, the following Examples are not to be construed to limit the scope of the present invention.

Hereinafter "%" means "% by weight", unless otherwise specified.

Preparation Example

According to the method described in Example 38 of Japanese Unexamined Patent Application, First Publication No. Hei 9-255659, 7-(3,5-dimethoxy-4-hydroxycinnamoylamino)-3-octyloxy-4-hydroxy-1-methyl-2(1H)-quinoline represented by the structural formula (I) (hereinafter referred merely to as a quinolinone derivative) was synthesized and, furthermore, a quinolinone derivative was obtained as a β-type crystal according to the method described in Reference Example 2 of Japanese Unexamined Patent Application, First Publication No. Hei 11-255649.

The method described above was conducted two or more times to obtain quinoline before grinding (hereinafter referred to as a quinolinone derivative (A) and a quinolinone derivative (B)).

The particle size distribution of the quinolinone derivative (A) was measured and differential scanning calorimetry (DCS) was conducted. As a result, the average particle diameter was 25.3 μm and particles having a particle diameter of 15 μm or less accounted for 9.9% or more of the totality of the particles, and the fusion enthalpy (ΔH) was 49.9 J/g or more.

In the same manner, the measurement was conducted with respect to the quinolinone derivative (B). As a result, the average particle diameter was 33.3 μm and particles having a particle diameter of 15 μm or less accounted for 0.6% or more of the totality of the particles, and the fusion enthalpy (ΔH) was 52.7 J/g or more.

Then, the quinolinone derivative (A) and quinoline (B) were ground by a jet grinder (A-0 Jet Mill: manufactured by Seishin Enterprise Co., Ltd.) (powder feed rate: about 0.75 g/min., air pressure: 6 to 7 kg/cm$^2$). The ground quinolinone derivatives thus obtained are referred to as Squinoline (A-1) and quinoline (B-1), respectively.

The particle size distribution of the resulting ground product of the quinolinone derivative was measured and differential scanning calorimetry (DSC) was conducted. The results are summarized in Table 1.

<Analytical Conditions>

Measurement of particle size distribution: The particle size distribution was automatically measured by AEROSIZER (manufactured by Central Scientific Commerce, Inc.).

DSC method: Using DSC7 (manufactured by Perkin Elmer Co.), the measurement was conducted at a temperature within a range from 25 to 250° C. under the conditions of a heating rate of 20° C./min. by a normal method.

TABLE 1

| Quinoline | Average particle diameter (μm) | Proportion (%) of particles having a particle diameter of 15 μm or less based on the totality of the particles | DSC Endothermic peak (° C.) | DSC Fusion enthalpy ΔH (J/g) |
|---|---|---|---|---|
| (A) | 25.3 | 9.9 | 151 | 49.9 |
| (A-1) | 4.5 | 100 | 147 | 47.7 |
| (B) | 33.3 | 0.6 | 150 | 52.7 |
| (B-1) | 6.6 | 95 | 146 | 51.6 |

As is apparent from the results shown in Table 1, the average particle diameter of the ground product of the quinolinone derivative was 10 μm or less. Also it was confirmed that particles having a particle diameter of 15 μm or less accounted for 100% of the totality of the particles. As is apparent from the results of the measurement of DSC, a drastic decrease in fusion enthalpy (ΔH) of the ground product was not observed as compared with the non-ground product.

Example 1 and Comparative Example 1

Figure 1:
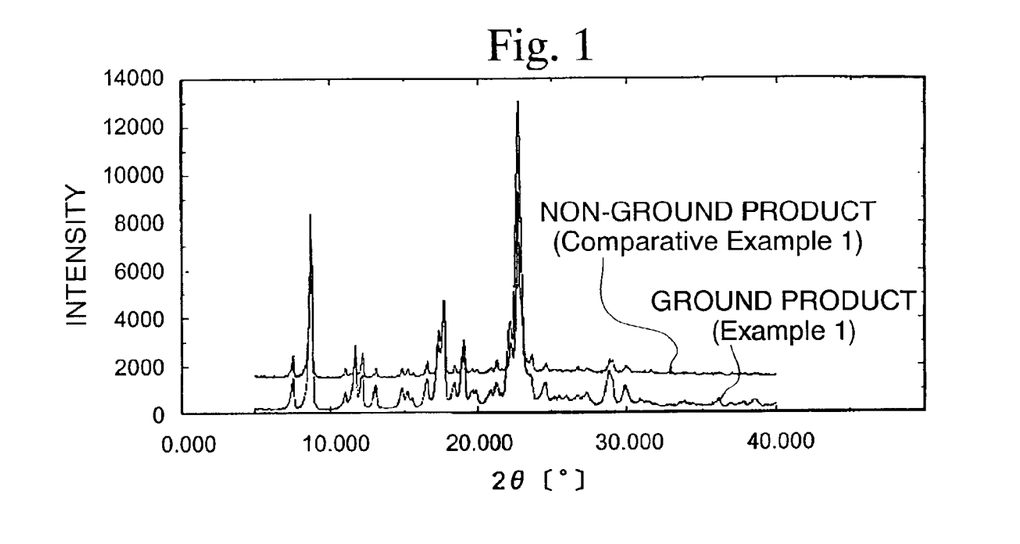
FIG. 1 is a graph showing powder X-ray diffraction patterns before and after grinding a quinolinone derivative.

With respect to the quinolinone derivative (A) (Comparative Example 1) and quinolinone derivative A-1 (Example 1), the powder X-ray diffraction was measured. The results are shown in FIG. 1.

Figure 2:
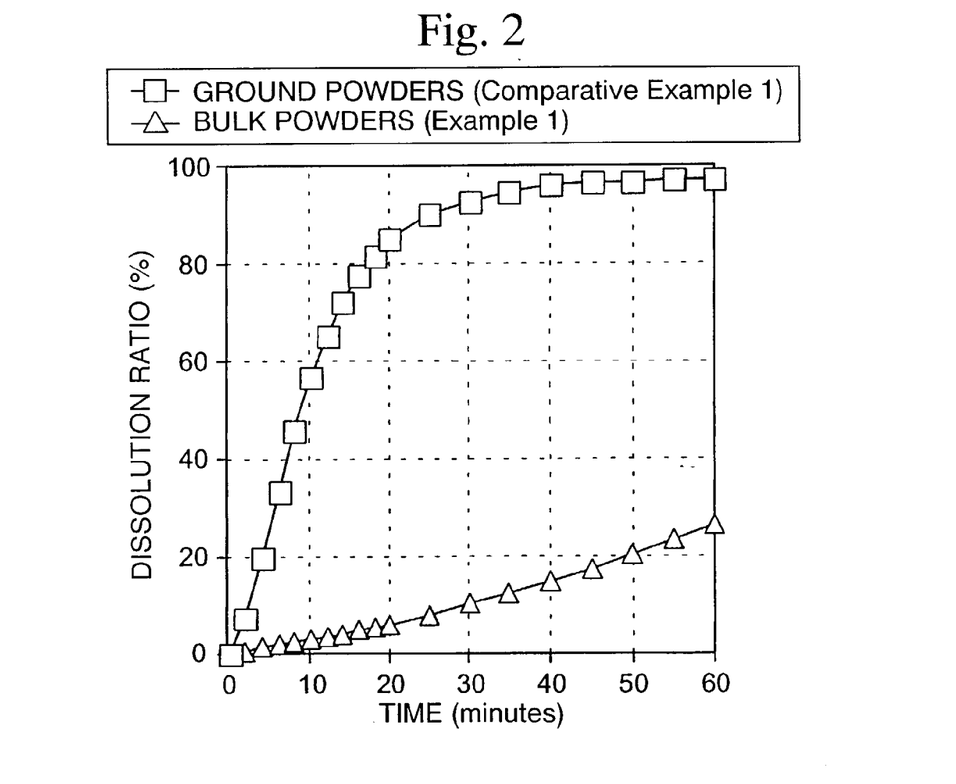
FIG. 2 is a graph showing a relationship between the dissolution time and the dissolution ratio before and after grinding a quinolinone derivative.

Furthermore, dissolution properties of these quinolinone derivatives were evaluated by the dissolution test (paddle method). The results are shown in FIG. 2.

Powder X-ray diffraction method: Using RINT-ULTIMA (manufactured by Rigaku Denki Kogyo Co., Ltd.), the measurement was conducted at a diffraction angle within a range from 5 to 40° under the conditions of Cu—Kα rays, 40 KV and 30 mA by the normal method.

Dissolution test method: According to the second method (paddle method) of the dissolution test method of The Pharmacopoeia of Japan, Fourteenth Edition, the measurement was conducted under the conditions of a paddle rotational speed of 50 rpm using 0.5% sodium lauryl sulfate as a test liquid.

The powder X-ray diffraction patterns of the non-ground product and the ground product agreed as shown in FIG. 1 and both maintained the β-type crystal. On the other hand, as shown in FIG. 2, the dissolution rate of the ground product drastically increased as compared with the non-ground product.

As is apparent from the results described above, the quinolinone derivative is finely ground by jet grinding while being inhibited from being converted into an amorphous state, thereby improving the dissolution rate.

Comparative Example 2

The quinolinone derivative (A) used in Comparative Example 1 was ground in an agate mortar for 30 minutes so as to reduce the particle diameter to 10 μm or less. With respect to the resulting quinolinone derivative, DSC was measured. As a result, it was confirmed that an endothermic peak due to fusion of the β-type crystal disappeared and the quinolinone derivative is in an amorphous state.

Examples 2 to 6 and Comparative Example 3

As the water-soluble polymer for coating the quinolinone derivative, for example, hydroxypropyl cellulose (HPC-L: manufactured by NIPPON SODA CO., LTD., viscosity: 6 to 10 cps) (Example 2), hydroxypropylmethyl cellulose (HPMC TC-5MW: manufactured by Shin-Etsu Chemical Co., Ltd.) (Example 3), pullulan (manufactured by Hayashibara Shoji, Inc.) (Example 4), sodium carboxymethyl cellulose (CMC-Na: manufactured by GOTOKU CHEMICAL COMPANY LTD.) (Example 5), and polyvinyl pyrrolidone (PVP: manufactured by GOKYO TRADING CO.) (Example 6) were used.

According to the formulation shown in Table 2, a quinolinone derivative (A-1, ground product), lactose (200M DMV), crystalline cellulose (Avicel PH101: manufactured by Asahi Kasei Corporation) and low-substitution-degree hydroxypropyl cellulose (L-HPC LH-31: manufactured by Shin-Etsu Chemical Co., Ltd.) were mixed in a mortar. Each of various aqueous solutions of the water-soluble polymers prepared previously by dissolving in a proper amount of water was added to the above composition (in the amount of 10 parts by weight based on 100 parts by weight of the quinolinone derivative) and the mixture was kneaded, classified using a screen No. 20 and then dried. The resulting particles were dried and then classified using a screen No. 35 to obtain quinolinone derivative particles surface-coated with various water-soluble polymers.

TABLE 2

|  | Example 2 | Example 3 | Example 4 | Example 5 | Example 6 | Comparative Example 3 |
|---|---|---|---|---|---|---|
| Water-soluble polymer | HPC-L | HPMC | Pullulan | CMC-Na | PVP | — |
| Composition Ground quinolinone derivative | 1 g | 1 g | 1 g | 1 g | 1 g | 1 g |
| Lactose | 0.5 g | 0.5 g | 0.5 g | 0.55 g | 0.5 g | — |
| Crystalline cellulose | 0.2 g | 0.2 g | 0.2 g | 0.2 g | 0.2 g | — |
| L-HPC (LH-31) | 0.2 g | 0.2 g | 0.2 g | 0.2 g | 0.2 g | — |
| HPC-L | 0.1 g | — | — | — | — | — |
| HPMC TC-5MW | — | 0.1 g | — | — | — | — |
| Pullulan | — | — | 0.1 g | — | — | — |
| CMC-Na | — | — | — | 0.05 g | — | — |
| PVP | — | — | — | — | 0.1 g | — |
| Total | 2 g | 2 g | 2 g | 2 g | 2 g | 1 g |

Dissolution properties of the resulting granules were evaluated by the dissolution test (flow-through cells method). According to the third dissolution test (flow-through cells method) of The Pharmacopoeia of Japan, Fourteenth Edition, the measurement was conducted under the conditions of a flow rate of about 7 ml using 1% polysolvate 80 as a test liquid. As a control, the dissolution rate of the ground product of the quinolinone derivative coated with no water-soluble polymer (Comparative Example 3) was also measured.

Figure 3:
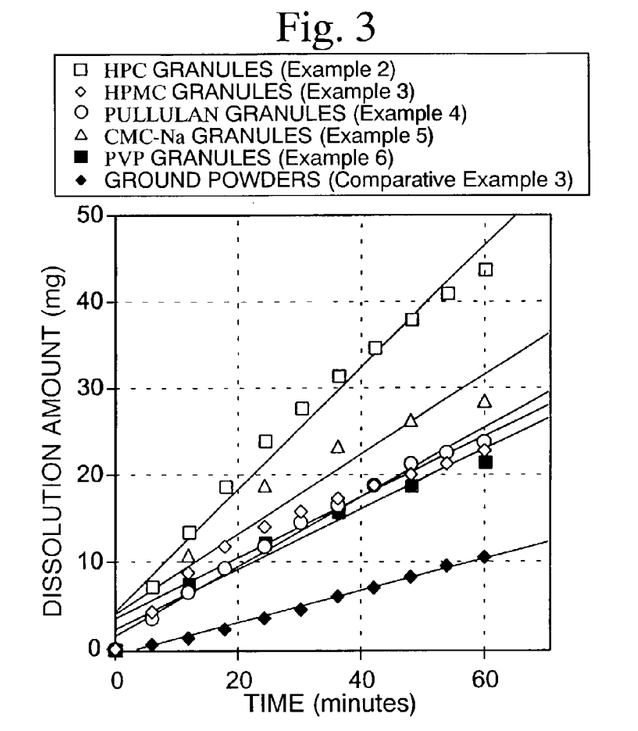
FIG. 3 is a graph showing a relationship between the dissolution time and the dissolution amount depending on the kind of a water-soluble polymer coated with a quinolinone derivative.

The results of the dissolution test of the ground products of the quinolinone derivatives surface-coated with various water-soluble polymers and the ground product of the quinolinone derivative coated with no water-soluble polymer are shown in FIG. 3. As is apparent from the results shown in FIG. 3, the ground products of the quinolinone derivatives surface-coated with various water-soluble polymers exhibit high dissolution rate as compared with the ground product of the quinolinone derivative coated with no water-soluble polymer, and therefore the surface coating with the water-soluble polymer is effective to improve the dissolution rate of the ground product of the quinolinone derivative. As is apparent from a comparison between various water-soluble polymers, the dissolution rate is remarkably improved when using HPC-L and CMC-Na.

Examples 7 to 11

According to the formulation shown in Table 3, a quinolinone derivative (A-1, ground product), lactose, crystalline cellulose and L-HPC were mixed in a mortar. An aqueous solution of HPC-L prepared by previously dissolving in a proper amount of water was added to the above composition so that the amount becomes 4 parts by weight (Example 7), 6 parts by weight (Example 8), 8 parts by weight (Example 9), 10 parts by weight (Example 10) and 12 parts by weight (Example 11) based on 100 parts by weight of the quinolinone derivative. The mixture was kneaded, classified using a No. 20 screen and then dried. After drying and classifying using screen No. 35, quinolinone derivative granules were obtained. The resulting quinolinone derivative granules were mixed with 0.5% magnesium stearate, and then 200 mg of the mixed powders were hydrostatically compressed under a pressure of 600 kg by a hydraulic press using a punch having a diameter of 8 mm and double R to obtain tablets.

quick dissolution properties (dissolution ratio is 75% or more within 60 minutes) are obtained when the amount of HPC-L is 10% or less.

Examples 12 to 18

According to the formulation shown in Table 4, a quinolinone derivative (A-1, ground product), lactose, crystalline cellulose (Avicel PH101) and various disintegrators were mixed in a mortar. Seven kinds of disintegrators such as low-substitution-degree hydroxypropyl cellulose (L-HPC LH-31: manufactured by Shin-Etsu Chemical Co., Ltd.) (Example 12), croscarmellose sodium (Ac-Di-Sol: manufactured by Asahi Kasei Corporation) (Example 13), carmellose (NS-300: manufactured by GOTOKU CHEMICAL COMPANY LTD.) (Example 14), carmellose calcium (ECG-505: manufactured by GOTOKU CHEMICAL COMPANY LTD.) (Example 15), partially pregelatinized starch (PCS: manufactured by Asahi Kasei Corporation) (Example 16), sodium carboxymethyl starch (PRIMOGEL: manufactured by MATSUTANI CHEMICAL INDUSTRY CO., LTD.) (Example 17) and crospovidone (COLIDONE CL:

TABLE 3

| | | Example 7 | Example 8 | Example 9 | Example 10 | Example 11 |
|---|---|---|---|---|---|---|
| Hydroxypropyl cellulose (HPC-L) | | 4% | 6% | 8% | 10% | 12% |
| Composition | Ground quinolinone derivative | 2.0 g | 2.0 g | 2.0 g | 2.0 g | 2.0 g |
| | Lactose | 1.12 g | 1.08 g | 1.04 g | 1.00 g | 0.96 g |
| | Crystalline cellulose | 0.4 g | 0.4 g | 0.4 g | 0.4 g | 0.4 g |
| | L-HPC (LH-31) | 0.4 g | 0.4 g | 0.4 g | 0.4 g | 0.4 g |
| | HPC-L | 0.08 g | 0.12 g | 0.16 g | 0.2 g | 0.24 g |
| | Total | 0.4 g | 0.4 g | 0.4 g | 0.4 g | 0.4 g |

Figure 4:
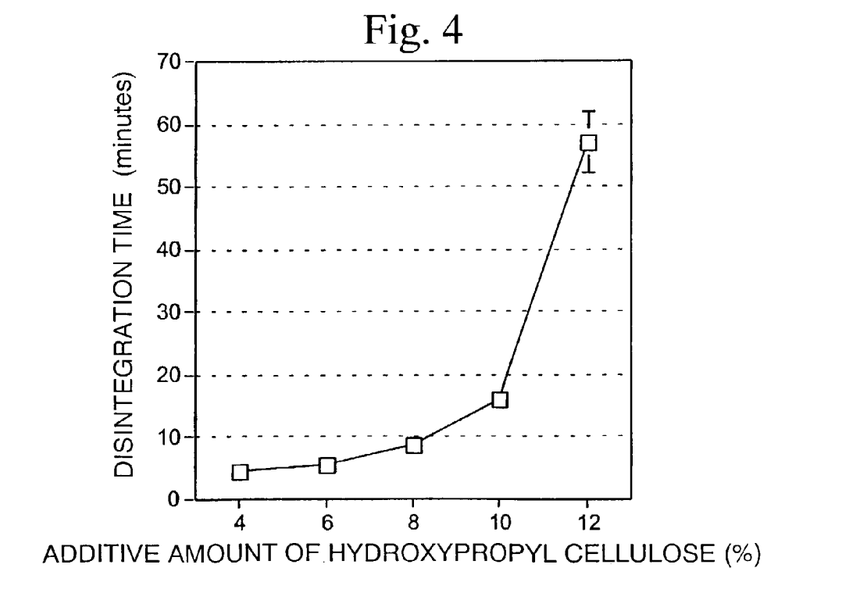
FIG. 4 is a graph showing a relationship between the additive amount of hydroxypropyl cellulose for coating a quinolinone derivative and the disintegration time of a quinolinone derivative pharmaceutical composition.
Figure 5:
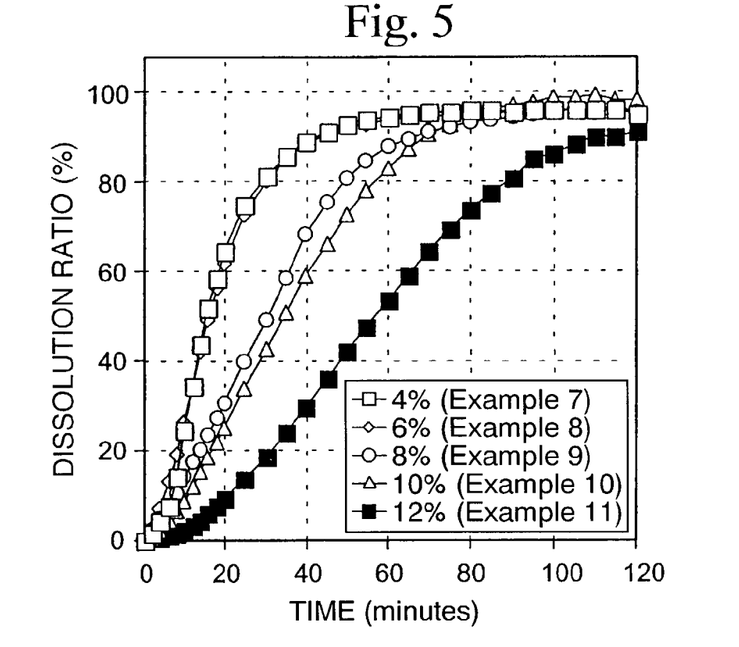
FIG. 5 is a graph showing a relationship between the dissolution ratio and the dissolution time of a quinolinone derivative pharmaceutical composition with a change in addition amount of hydroxypropyl cellulose for coating a quinolinone derivative.

According to the disintegration test of The Pharmacopoeia of Japan, Fourteenth Edition, the disintegration time of the resulting tablets was measured by using water as a test liquid (n=3). The results of the disintegration test of the resulting tablets are shown in FIG. 4. According to the second dissolution test of The Pharmacopoeia of Japan, Fourteenth Edition (paddle method), the dissolution test was conducted under the conditions of a paddle rotational speed of 50 rpm using 0.5% sodium lauryl sulfate as a test liquid. The results of the dissolution test of the resulting tablets are shown in FIG. 5.

As is apparent from the results shown in FIG. 4, comparatively quick disintegration (within 30 minutes) is obtained when the amount of HPC-L is 10% or less. As is apparent from the results shown in FIG. 5, comparatively manufactured by BASF Co.) (Example 18) were used and each of them was mixed with the quinolinone derivative in the amount of 20%.

An aqueous solution of HPC-L prepared by previously dissolving in a proper amount of water was added to the above composition so that the amount becomes the amount shown in Table 4. The mixture was kneaded, classified using a No. 20 screen and then dried. After drying and classifying using a screen No. 35, quinolinone derivative granules were obtained. The resulting quinolinone derivative granules were mixed with 0.5% magnesium stearate, and then 200 mg of the mixed powders were hydrostatically compressed under a pressure of 600 kg by a hydraulic press using a punch having a diameter of 8 mm and double R to obtain tablets.

TABLE 4

| | | Example 12 | Example 13 | Example 14 | Example 15 | Example 16 | Example 17 | Example 18 |
|---|---|---|---|---|---|---|---|---|
| | Integrator | HPC-L | Ac-Di-Sol | NS-300 | ECG-505 | PCS | PRIMOGEL | COLIDONE CL |
| Composition | Ground quinolinone derivative | 1.5 g | 1.5 g | 1.5 g | 1.5 g | 1.5 g | 1.5 g | 1.5 g |
| | Lactose | 0.765 g | 0.765 g | 0.765 g | 0.765 g | 0.765 g | 0.765 g | 0.765 g |

TABLE 4-continued

|  | Example 12 | Example 13 | Example 14 | Example 15 | Example 16 | Example 17 | Example 18 |
|---|---|---|---|---|---|---|---|
| Crystalline cellulose | 0.3 g | 0.3 g | 0.3 g | 0.3 g | 0.3 g | 0.3 g | 0.3 g |
| HPC-L | 0.135 g | 0.135 g | 0.135 g | 0.135 g | 0.135 g | 0.135 g | 0.135 g |
| L-HPC (LH-31) | 0.3 g | — | — | — | — | — | — |
| Ac-Di-Sol | — | 0.3 g | — | — | — | — | — |
| NS-300 | — | — | 0.3 g | — | — | — | — |
| ECG-505 | — | — | — | 0.3 g | — | — | — |
| PCS | — | — | — | — | 0.3 g | — | — |
| PRIMOGEL | — | — | — | — | — | 0.3 g | — |
| COLIDONE CL | — | — | — | — | — | — | 0.3 g |
| Total | 3.0 g | 3.0 g | 3.0 g | 3.0 g | 3.0 g | 3.0 g | 3.0 g |

Figure 6:
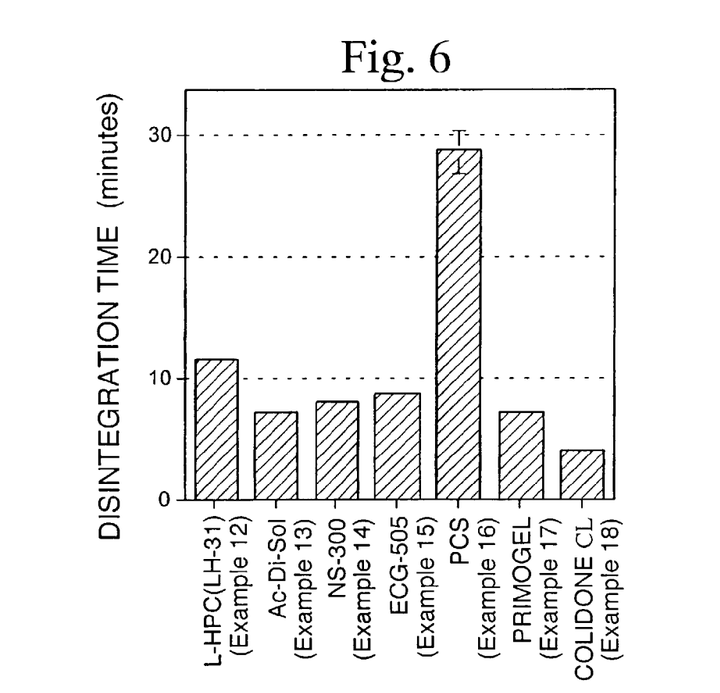
FIG. 6 is a graph showing a relationship between the kind of disintegrator added in a quinolinone derivative pharmaceutical composition and the disintegration time of the quinolinone derivative pharmaceutical composition.
Figure 7:
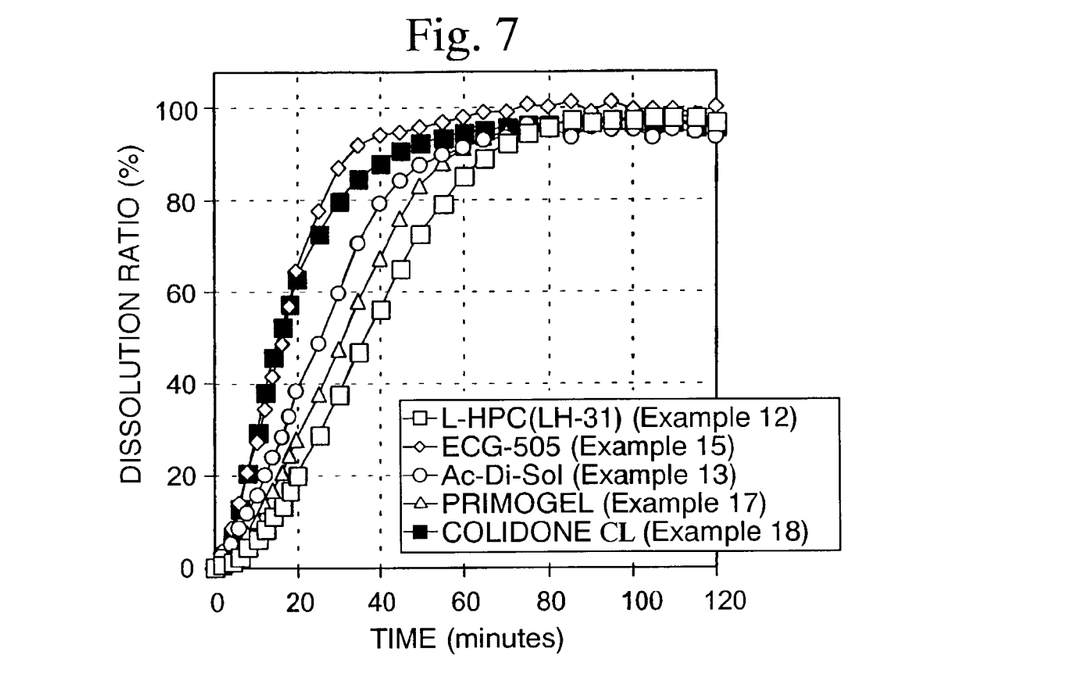
FIG. 7 is a graph showing a relationship between the kind of disintegrator added in a quinolinone derivative pharmaceutical composition and the disintegration time and the dissolution ratio of the quinolinone derivative pharmaceutical composition.

According to the disintegration test of The Pharmacopoeia of Japan, Fourteenth Edition, the disintegration time of the resulting tablets was measured by using water as a test liquid (n=3). The results of the disintegration test of the resulting tablets are shown in FIG. 6. With respect to the tablets that exhibited good dispersibility in the disintegration test, the dissolution test was conducted. According to the second dissolution test (paddle method) of The Pharmacopoeia of Japan, Fourteenth Edition, the dissolution test was conducted under the conditions of a paddle rotational speed of 50 rpm using 0.5% sodium lauryl sulfate as a test liquid. The results of the dissolution test of the resulting tablets using L-HPC, Ac-Di-Sol, ECG-505, PRIMOGEL and COLIDONE CL, which exhibited good dispersibility, are shown in FIG. 7.

As is apparent from the results shown in FIG. 6, quick disintegration (within 30 minutes) is obtained in the case of all disintegrators. In the case of PCS and NS-300, the dispersibility was poor because of coarse dispersed particles upon disintegration. As is apparent from the results shown in FIG. 7, the resulting tablets exhibit quick dissolution properties (dissolution ratio is 75% or more within 60 minutes) when using any disintegrator and a large dissolution rate is obtained in the case of Ac-Di-Sol, COLIDONE CL and ECG-505.

Examples 19 to 21

According to the formulation shown in Table 5, a quinolinone derivative (A-1, ground product), lactose, crystalline cellulose and Ac-Di-Sol were mixed in a vertical granulator (VG-01: manufactured by POWREX CORPORATION). Regarding Ac-Di-Sol, three kinds having final concentrations of 10% (Example 19), 15% (Example 20) and 20% (Example 21) were prepared. An aqueous solution of HPC-L prepared by previously dissolving in a proper amount of water was added to the above composition so that the amount becomes the amount shown in Table 5. The mixture was kneaded, sifted in a speed mill (ND-10, manufactured by OKADA SEIKO CO., LTD.) and then vacuum-dried. After drying and classifying using a No. 20 screen, quinolinone derivative granules were obtained. The resulting quinolinone derivative granules were mixed with 0.5% magnesium stearate, and then 200 mg of the mixed powders were hydrostatically compressed under a pressure of 600 kg by a single punch tableting machine (N-20, manufactured by OKADA SEIKO CO., LTD.) using a punch having a diameter of 8 mm and 10R to obtain tablets.

TABLE 5

|  |  | Example 19 10% | Example 20 15% | Example 21 20% |
|---|---|---|---|---|
|  | Ac-Di-Sol |  |  |  |
| Composition | Ground quinolinone derivative | 150 g | 150 g | 150 g |
|  | Lactose | 91.5 g | 84 g | 76.5 g |
|  | Crystalline cellulose | 30 g | 30 g | 30 g |
|  | HPC-L | 13.5 g | 13.5 g | 13.5 g |
|  | Ac-Di-Sol | 15 g | 22.5 g | 30 |
|  | Total | 300 g | 300 g | 300 g |

Figure 8:
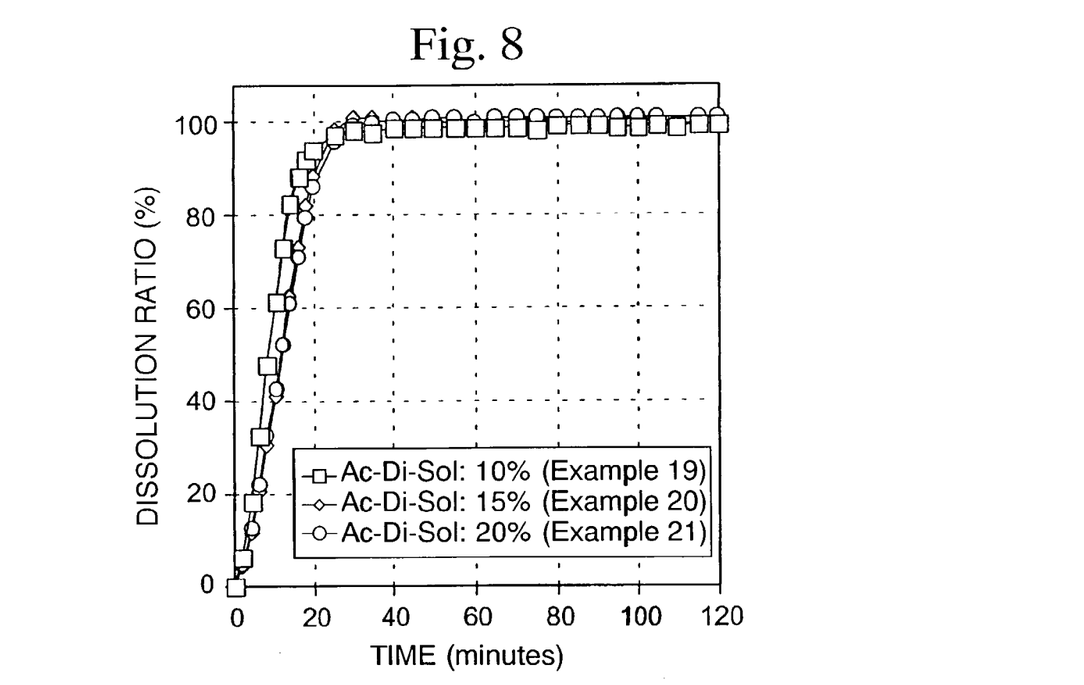
FIG. 8 is a graph showing a relationship between the dissolution time and the dissolution ratio of a quinolinone derivative pharmaceutical composition to which Ac-Di-Sol is added as a disintegrator.

According to the disintegration test of The Pharmacopoeia of Japan, Fourteenth Edition, the disintegration time of the resulting tablets was measured by using water as a test liquid (n=3). The results of the disintegration test of the resulting tablets are shown in Table 6. According to the second dissolution test (paddle method) of The Pharmacopoeia of Japan, Fourteenth Edition, the dissolution test was conducted under the conditions of a paddle rotational speed of 50 rpm using 0.5% sodium lauryl sulfate as a test liquid. The results of the dissolution test of the resulting tablets are shown in FIG. 8.

TABLE 6

|  | Sample (Ac-Di-Sol) | Disintegration time |
|---|---|---|
| Example 19 | 10% | 8.6 min. |
| Example 20 | 15% | 8.0 min. |
| Example 21 | 20% | 7.1 min. |

As is apparent from the results shown in Table 6, the resulting tablets exhibit quick disintegration (within 30 minutes) when the amount of Ac-Di-Sol is within a range from 10 to 20%. As is apparent from the results shown in FIG. 8, quick dissolution properties (dissolution ratio is 75% or more within 60 minutes) are obtained when the amount of Ac-Di-Sol is within a range from 10 to 20%.

Example 22 and Comparative Examples 4 to 5

Capsule No. 1 filled with each of the quinolinone derivative (B, non-ground product) (Comparative Example 4), a quinolinone derivative (B-1, ground product) (Comparative Example 5) and HPC granules (Example 22) of the quinolinone derivative prepared in Example 2 was orally administered to nine beagle dogs (male, aged 12 months) fasted for 24 hours at a dose of 10 mg/kg of the quinolinone derivative. After oral administration, 30 ml of distilled water was orally administered. After oral administration, 2.5 ml of blood was collected from the antebrachial vein over time and was then centrifuged to obtain blood plasma. After adding the one-fold amount of acetonitrile to blood serum to remove protein, the amounts of quinolinone derivative and its metabolite were determined by using HPLC.

From the quantitatively determined values of the quinolinone derivative and its metabolite immediately after collecting blood, an average value of a maximum concentration in blood (Cmax) and an average value of an area under a curve of concentration in blood vs time (AUC) were determined. The results are shown in Table 7. As is apparent from the results shown in Table 7, tendency of an improvement in absorbability due to grinding was observed in the ground product of the quinolinone derivative because Cmax increased by 9 times and AUC increased by 8.7 times as compared with the non-ground product. It is found that the effect of the coating of the surface of the quinolinone derivative with HPC is observed in the HPC granules of the quinolinone derivative because Cmax increased by 16.5 times and AUC increased by 13.3 times as compared with the non-ground product and, moreover, Cmax increased by 1.8 times and AUC increased by 1.5 times as compared with the ground product. As is apparent from the results described above, grinding and surface coating with the water-soluble polymer improve the absorbability in the digestive tract. In Table 7, the symbol "**" indicates that the results of t-test is as follows: $p<0.01$.

TABLE 7

| | Samples | Cmax (ng/ml) | AUC (ng · hr/ml) |
|---|---|---|---|
| Comparative Example 4 | Non-ground quinolinone derivative | 152.3 | 872.0 |
| Comparative Example 5 | Ground quinolinone derivative | 1364.6 | 7580.5 |
| Example 22 | HPC-L coated particles | 2516.9** | 11605.5** |

Example 23 and Comparative Example 6

According to the formulation shown in Table 8, a quinolinone derivative (B, non-ground product) (Comparative Example 6) or a quinolinone derivative (B-1, ground product) (Example 23), lactose, crystalline cellulose and Ac-Di-Sol were mixed in a mortar. Separately, an aqueous solution of HPC-L prepared by dissolving in a proper amount of water was added to the above composition so that the amount becomes the amount shown in Table 8. The mixture was kneaded, classified using a with No. 20 screen and then dried. After drying and classifying using a screen No. 35, granules using non-ground and ground quinolinone derivatives were obtained.

TABLE 8

| | | Comparative Example 6 Non-ground quinolinone derivative | Example 23 Ground quinolinone derivative |
|---|---|---|---|
| Composition | Non-ground quinolinone derivative | 5 g | — |

TABLE 8-continued

| | | Comparative Example 6 Non-ground quinolinone derivative | Example 23 Ground quinolinone derivative |
|---|---|---|---|
| | Ground quinolinone derivative | — | 5 g |
| | Lactose | 3.05 g | 3.05 g |
| | Avicel PH101 | 1 g | 1 g |
| | HPC-L | 0.45 g | 0.45 g |
| | Ac-Di-Sol | 0.5 g | 0.5 g |
| | Total | 10 g | 10 g |

Capsule No. 1 filled with each of granules using the quinolinone derivative (B, non-ground product) and granules using the quinolinone derivative (B-1, ground product) were orally administered to nine beagle dogs (male, aged 12 months) fasted for 24 hours at a dose of 10 mg/kg of the quinolinone derivative. After oral administration, 30 ml of distilled water was orally administered. After oral administration, 2.5 ml of blood was collected from the antebrachial vein over time and was then centrifuged to obtain blood plasma. After adding the one-fold amount of acetonitrile to blood serum to remove protein, the amounts of quinolinone derivative and its metabolite were determined by using HPLC.

From the quantitatively determined values of the quinolinone derivative and its metabolite immediately after collecting blood, an average value of a maximum concentration in blood (Cmax) and an average value of an area under a curve of concentration in blood vs time (AUC) were determined. The results are shown in Table 9. As is apparent from the results shown in Table 9, the absorbability improving effect was recognized in the granules using the ground product of the quinolinone derivative because Cmax increased by 3.9 times and AUC increased by 4.3 times as compared with the granules using the non-ground product. As is apparent from the results described above, control of the particle diameter of bulk is an important factor in the manufacture of the preparation. In Table 9, the symbol "**" indicates that the results of t-test are as follows: $p<0.05$.

TABLE 9

| | | Cmax (ng/ml) | AUC (ng · hr/ml) |
|---|---|---|---|
| Comparative Example 6 | Particles using non-ground product | 331.2 | 2021.3 |
| Example 23 | Particles using ground product | 1289.1** | 8620.2** |

Examples 24 to 26

According to the formulation shown in Table 10, a quinolinone derivative (B-1, ground product), lactose, crystalline cellulose (Avicel PH101), Ac-Di-Sol and various surfactants were mixed in a mortar. As the surfactant, for example, dioctyl sodium sulfosuccinate (manufactured by Aldrich Co.) (Example 24) and sodium lauryl sulfate (manufactured by KANTO KAGAKU CO., LTD.) (Example 25) were used. The composition containing no surfactant (Example 26) was also prepared. An aqueous solution of HPC (manufactured by NIPPON SODA CO., LTD., viscosity: 3 to 5.9 cps) prepared by dissolving in a proper amount of water was added to the above composition so that the amount becomes the amount shown in Table 10. The mixture was kneaded, dried and then classified to obtain granules of the quinolinone derivatives. The resulting granules were mixed with magnesium stearate, and then 200 mg of the mixed powders were hydrostatically compressed under a pressure of 600 kg by a hydraulic press using a punch having a diameter of 8 mm to obtain tablets.

TABLE 10

|  |  | Example 24 | Example 25 | Example 26 |
|---|---|---|---|---|
| Composition | Ground quinolinone derivative | 50.0% | 50.0% | 50.0% |
|  | Lactose | 29.9% | 25.0% | 30.0% |
|  | Avicel PH101 | 10.0% | 10.0% | 10.0% |
|  | Ac-Di-Sol | 5.0% | 5.0% | 5.0% |
|  | Dioctyl sodium sulfosuccinate | 0.1% | — | — |
|  | Sodium lauryl sulfate | — | 5.0% | — |
|  | HPC | 4.5% | 4.0% | 4.5% |
|  | Magnesium stearate | 0.5% | 0.5% | 0.5% |

According to the second dissolution test (paddle method) of The Pharmacopoeia of Japan, Fourteenth Edition, dissolution properties of the resulting tablets were evaluated by the dissolution test under the conditions of a paddle rotational speed of 100 rpm using 0.2% sodium lauryl sulfate as a test liquid. The results are shown in FIG. 9.

Figure 9:
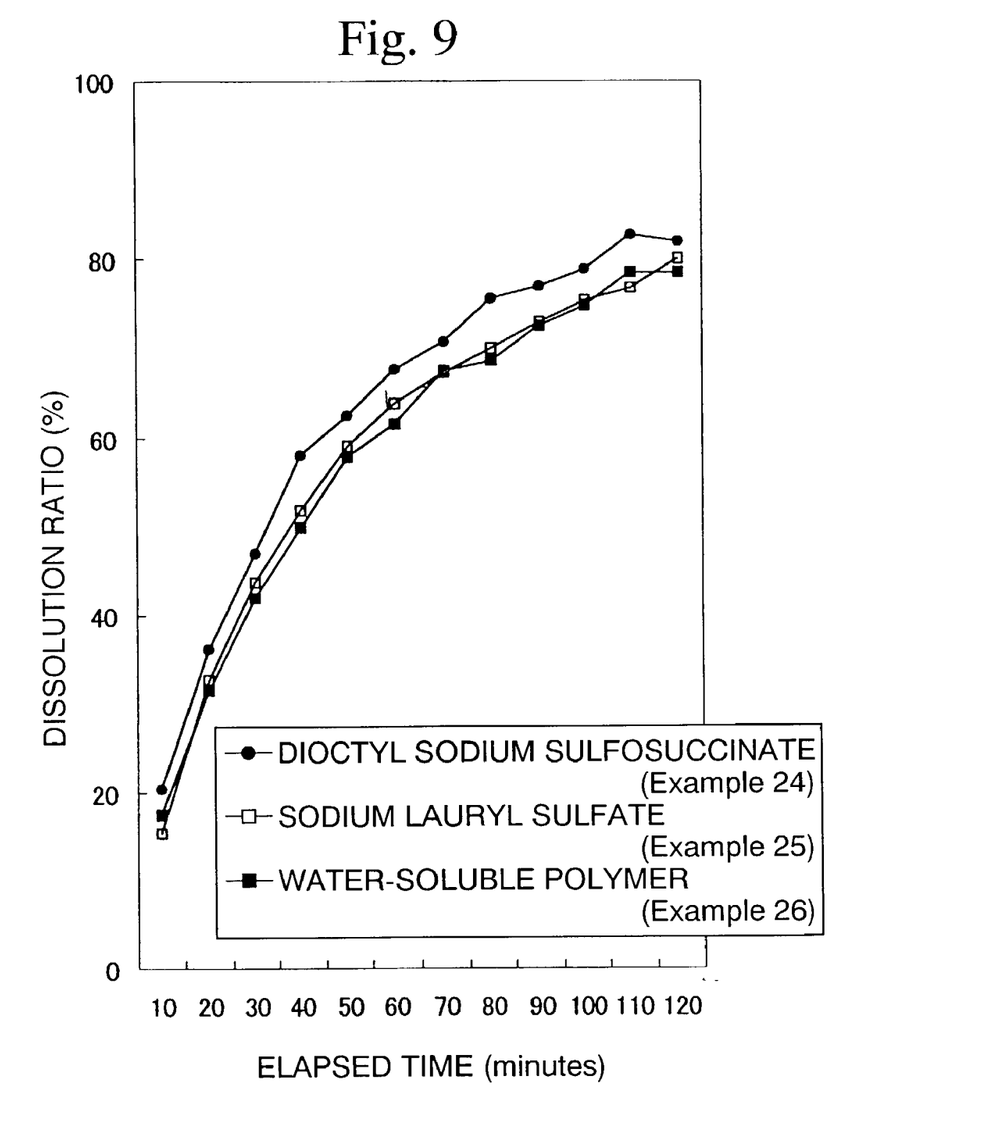
FIG. 9 is a graph showing a relationship between the dissolution time and the dissolution amount of a quinolinone derivative pharmaceutical composition coated with a water-soluble polymer and a surfactant.

As is apparent from the results shown in FIG. 9, the tablets coated with the water-soluble polymer and the surfactant exhibited more preferred dissolution ratio as compared with the tablets coated only with the water-soluble polymer and therefore surface coating with the water-soluble polymer and the surfactant is effective to improve the dissolution ratio of the ground product of the quinolinone derivative.

Example 27 and Example 28

According to the formulation shown in Table 11, a quinolinone derivative (B-1, ground product), dioctyl sodium sulfosuccinate, Ac-Di-Sol, lactose, crystalline cellulose and L-ascorbic acid were mixed in a mortar. An aqueous solution of HPC prepared by dissolving in a proper amount of water was added to the above composition so that the amount becomes the amount shown in Table 11. The mixture was kneaded, dried and then classified to obtain quinolinone derivative granules. The resulting granules were mixed with magnesium stearate, and then 200 mg of the mixed powders were hydrostatically compressed under a pressure of 200 kg by a hydraulic press using a punch having a diameter of 8 mm and 10R to obtain tablets (Example 27).

Also a quinolinone derivative (B-1, ground product), Ac-Di-Sol, lactose, crystalline cellulose and L-ascorbic acid were mixed in a mortar. An aqueous solution of HPC-L prepared by dissolving in a proper amount of water was added to the above composition so that the amount becomes the amount shown in Table 11. The mixture was kneaded, dried and then classified to obtain quinolinone derivative granules (Example 28)

TABLE 11

|  |  | Example 27 | Example 28 |
|---|---|---|---|
| Composition | Quinolinone derivative ground product | 50.0% | 50.0% |
|  | Lactose | 29.7% | 30.0% |
|  | Avicel PH101 | 10.0% | 10.0% |
|  | Ac-Di-Sol | 5.0% | 5.0% |
|  | Dioctyl sodium sulfosuccinate | 0.3% | — |
|  | HPC | 4.5% | 4.5% |
|  | Magnesium sterate | 0.5% | 0.5% |

The preparation in the dosage form of capsules or tablets was orally administered to six rhesus monkeys (male, body weight of about 5 to 6 kg) acclimatized for a week at a dose of 200 mg/monkey of the quinolinone derivative. After oral administration, 50 ml of distilled water was orally administered. After oral administration, 2.0 ml of blood was collected from the femoral vein over time and was then centrifuged to obtain blood plasma. After adding the one-fold amount of acetonitrile to blood serum to remove protein, the amounts of quinolinone derivative and its metabolite were determined by using HPLC.

From the quantitatively determined values of the quinolinone derivative and its metabolite immediately after collecting blood, an average value of a maximum concentration in blood (Cmax) and an average value of an area under a curve of concentration in blood vs time (AUC) were determined. The results are shown in Table 12. As is apparent from the results shown in Table 12, further absorbability improving effect was recognized in the tablets obtained by coating the ground product of the quinolinone derivative with the water-soluble polymer and the surfactant because Cmax increased by 2.3 times and AUC increased by 2.1 times as compared with the tablets coated with the water-soluble polymer. As is apparent from the results described above, the quinolinone derivative particles are preferably coated with the water-soluble polymer and the surfactant in order to improve the absorbability. In Table 12, the symbol "**" indicates that the results of t-test are as follows: $p<0.05$.

TABLE 12

|  | Cmax (ng/ml) | AUC (ng · hr/ml) |
|---|---|---|
| Example 28 | 2185 | 31631 |
| Example 27 | 5151** | 68906** |

What is claimed is:
1. A quinolinone derivative pharmaceutical composition comprising a quinolinone derivative represented by the structural formula (I)

(I)

wherein the quinolinone derivative is in the form of particles, which have an average particle diameter of 0.5 to 10 μm and such a particle size distribution that particles having a particle diameter of 15 μm or less account for 90% or more of the totality of the particles, and also have a fusion enthalpy of 30 J/g or more, and the surface of the particles are coated with a water-soluble composition containing a water-soluble polymer.

2. The quinolinone derivative pharmaceutical composition according to claim 1, wherein the water-soluble polymer is a cellulose derivative.

3. The quinolinone derivative pharmaceutical composition according to claim 1, wherein the water-soluble composition contains a water-soluble polymer and a surfactant.

4. The quinolinone derivative pharmaceutical composition according to claim 3, wherein the surfactant is an anionic surfactant.

5. The quinolinone derivative pharmaceutical composition according to any one of claims 1 to 4, further comprising a disintegrator.

6. The quinolinone derivative pharmaceutical composition according to claim 5, wherein the disintegrator is at least one kind selected from the group consisting of croscarmellose sodium, low-substitution-degree hydroxypropyl cellulose, carmellose calcium, sodium carboxymethyl starch and crospovidone.

7. A process for producing a quinolinone derivative pharmaceutical composition, which comprises the first step of grinding a quinolinone derivative represented by the structural formula (I)

into particles, which have an average particle diameter of 0.5 to 10 μm arid such a particle size distribution that particles having a particle diameter of 15 μm or less account for 90% or more of the totality of the particles, and also have a fusion enthalpy of 30 J/g or more; and the step of coating the particles obtained in the first step with a water-soluble composition containing a water-soluble polymer.

8. The process for producing a quinolinone derivative pharmaceutical composition according to claim 7, wherein the grinding is conducted by a jet grinding method.

9. The process for producing a quinolinone derivative pharmaceutical composition according to claim 7, wherein the water-soluble composition contains a water-soluble polymer and a surfactant.

* * * * *